(12) United States Patent
Anderson

(10) Patent No.: US 9,250,171 B2
(45) Date of Patent: Feb. 2, 2016

(54) KIT FOR PERFORMING ADHESIVE AUDITS AND A METHOD FOR DOING THE SAME

(71) Applicant: John T Anderson, Mahtomedi, MN (US)

(72) Inventor: John T Anderson, Mahtomedi, MN (US)

(73) Assignee: H.B. Fuller Company, St. Paul, MN (US)

( * ) Notice: Subject to any disclaimer, the term of this patent is extended or adjusted under 35 U.S.C. 154(b) by 316 days.

(21) Appl. No.: 13/650,256

(22) Filed: Oct. 12, 2012

(65) Prior Publication Data

US 2013/0298660 A1    Nov. 14, 2013

Related U.S. Application Data

(60) Provisional application No. 61/644,742, filed on May 9, 2012.

(51) Int. Cl.
| | | |
|---|---|---|
| *G01N 5/00* | (2006.01) | |
| *G01N 1/28* | (2006.01) | |
| *G01N 19/04* | (2006.01) | |
| *G01N 5/04* | (2006.01) | |

(52) U.S. Cl.
CPC ............... *G01N 5/00* (2013.01); *G01N 1/2813* (2013.01); *G01N 19/04* (2013.01); *G01N 5/04* (2013.01); *Y10T 428/1352* (2015.01)

(58) Field of Classification Search
CPC ....... G01N 19/04; G01N 5/00; G01N 1/2813; G01N 2001/028
See application file for complete search history.

(56) References Cited

U.S. PATENT DOCUMENTS

| | | | | |
|---|---|---|---|---|
| 5,708,046 | A * | 1/1998 | Jones et al. | 522/99 |
| 5,844,007 | A * | 12/1998 | Kijima et al. | 521/98 |
| 6,026,680 | A | 2/2000 | Mann | |
| 6,419,915 | B1 | 7/2002 | Stein | |
| 6,541,109 | B1 * | 4/2003 | Kumar et al. | 428/352 |
| 6,703,120 | B1 | 3/2004 | Ko et al. | |
| 7,033,099 | B2 * | 4/2006 | Moutinho | 401/6 |
| 8,541,087 | B2 * | 9/2013 | Taya et al. | 428/64.1 |
| 2005/0038183 | A1 | 2/2005 | Ahn et al. | |
| 2005/0050661 | A1 * | 3/2005 | McKay | A47L 25/005 15/104.002 |
| 2007/0206249 | A1 * | 9/2007 | Phillips et al. | 359/2 |
| 2008/0004203 | A1 * | 1/2008 | Scheuing et al. | 510/475 |
| 2011/0017701 | A1 * | 1/2011 | Soliman | 215/381 |

FOREIGN PATENT DOCUMENTS

| | | |
|---|---|---|
| WO | WO 03/052020 | 6/2003 |
| WO | WO 2010021201 A1 * | 2/2010 |
| WO | WO 2012/003153 | 1/2012 |

OTHER PUBLICATIONS

Nagy, Keith, "Where Do We Go from Here?" Sep. 1, 2011, http://www.adhesivesmag.com/articles/89991-where-do-we-go-from-here-.*

* cited by examiner

*Primary Examiner* — Paul West
(74) *Attorney, Agent, or Firm* — Kristi Halloran; Kirsten Stone

(57) ABSTRACT

This invention is directed to a kit for performing adhesive audits and a method of doing the same. The kit and method can be used to improve the speed and ease with which adhesive audits are performed.

10 Claims, No Drawings

KIT FOR PERFORMING ADHESIVE AUDITS AND A METHOD FOR DOING THE SAME

CROSS-REFERENCE TO RELATED APPLICATIONS

This application claims the benefit of U.S. Provisional Application No. 61/644,742, filed May 9, 2012 and incorporated herein.

BACKGROUND

Adhesives are often used to bond substrates together so as to maintain the two substrates in a fixed relation to each other. In the area of industrial adhesives, adhesives (e.g. hot melt adhesives) are commonly used to bond together a wide variety of articles including e.g. cases, cartons, filters and disposable articles. Makers of these articles often switch between various adhesive suppliers based on criteria such as cost and performance or alternately are interested in optimizing the application of a current adhesive.

Prior to moving to a new adhesive or to optimize application of a current adhesive it is common to perform an audit to assist the user in optimizing the adhesive application amount per item (e.g. filter, case or carton).

In the manufacture of cases or cartons, adhesive audits are commonly performed using painter's tape to allow adhesive release for weight determination. Adhesive application amount can be then optimized to a specified weight target or range. Painter's tape is applied to the areas of the unfilled case or carton to which the adhesive is to be applied. The case or carton is then processed through the filling and adhesive application line (e.g. packaging line). At the end of the line, the case or carton is disassembled and the cooled adhesive is pulled from the painters tape and weighed to determine the adhesive application amount per case/carton.

Applying tape is a time consuming process and some adhesives with aggressive bonding characteristics do not pull easily from the tape but rather stick in spots which can reduce the accuracy of the audit.

It would be desirable to have a less time consuming way of performing an adhesive audit. Further, it would be desirable to have a material that even aggressive bonding adhesives could be pulled easily from but yet enables the article bonded to stay intact, or when the article is a case or carton, for the case or carton to stay together through the filling step and the adhesive application line.

SUMMARY

In one aspect, the invention features a kit for performing an adhesive audit, said kit including a container containing a release coating comprising silicone and, directions for performing the adhesive audit. In one embodiment, the release coating is a water based release coating. In another embodiment, the directions for performing the adhesive audit are packaged together with the container containing a release coating. In some embodiments, the release coating includes polydimethyl siloxane. In other embodiments, the release coating has a solids content of less than 30% by weight. In one embodiment, the release coating further comprises a second polymer. In some embodiments, the second polymer is an acrylic polymer. In other embodiments, the release coating further comprises a colorant. In another embodiment, the release coating has FDA approval under Title 21, Chapter 1, Subchapter B, Part 175, Subpart B, Section 175.105.

In one embodiment, the container holds no more than 3.4 ounces. In another embodiment, the container includes a plastic container equipped with a sponge applicator.

In another aspect, the invention features a kit for performing an adhesive audit, said kit comprising a plastic container equipped with an applicator at one end, said container containing a release coating that is liquid at room temperature.

In another aspect, the invention features a method of performing an adhesive audit on a substrate, the method including: obtaining a release coating that is liquid at room temperature, applying the release coating to substrate areas to be bonded, bonding the substrate through the substrate areas to be bonded, disassembling the substrate, removing the adhesive from the substrate with release coating, and weighing the adhesive removed to determine the amount applied per unit. In one embodiment, the substrate comprises cellulose. In another embodiment, the unit is a filter, bag, box, case, carton or tray. In some embodiments, the release coating is a water based release coating.

In one embodiment, the release coating comprises polydimethylsiloxane. In some embodiments, the release coating has a solids content of less than 30% by weight. In another embodiment, the release coating has release properties within 2 minutes after application and maintains those properties for at least one day. In one embodiment, the release coating has an Application Ease rating of Easy.

The inventor has now discovered that certain release coatings can be used to replace the painters tape and improve the speed and ease with which adhesive audits are performed.

DETAILED DESCRIPTION

Release Coating

The release coating can be a liquid, a gel, a semi-solid or a solid at room temperature. In a preferred embodiment, the release coating is a liquid at room temperature. The release coating can be 100% solids; alternately the release coating can be suspended in a carrier (e.g. water or solvent).

The release coating can have FDA approval under Title 21, Chapter 1, Subchapter B, Part 175, Subpart B, Section 175.105. This is particularly desirable when the release coating is used to perform an audit on a food packaging line.

When, the release coating is suspended in water; it is referred to as water based release coating. The water based release coating can be a dispersion, emulsion or solution. The water based release coating has a solids content of less than or equal to about 60% by weight, less or equal to about 40% by weight, less than 30% by weight, less than or equal to about 20% by weight, less than or equal to about 15% by weight, less than or equal to about 10% by weight, between about 5% by weight and 40% by weight, between about 5% by weight and 30% by weight, or even between about 7.5% and 20% by weight.

The release coating contains a release agent. The release agent can include metallic stearates (e.g. zinc stearate), flourocarbons (e.g. polytetrafluoroethylene (PTFE)), organic oils and greases (e.g. lecithin), waxes (e.g. polyethylene) and polymeric organosilicone compounds (often referred to as a silicone polymers).

The silicone polymer can be polydimethyl siloxane (PDMS). Useful water based polydimethyl siloxane polymers include RELEASE COAT 30 and RELEASE COAT 40 both available from Michelman, Inc (Cincinnati, Ohio).

The silicone polymer can be further diluted with water in order to improve adhesion of the adhesive to the release coated board stock. It is important that the adhesive stick well enough to the coating to enable the unit (e.g. case or carton) to get through the assembly and adhesive application process yet be fairly easy to pull apart and remove the adhesive once the adhesive has set.

The water based release coating can further include a second water based polymer different from the silicone polymer. The second water based polymer can also be used to adjust the adhesion of the adhesive to the coating.

The second polymer can be any polymer that improves the adhesion of the adhesive to the water based release coating. Representative examples of such polymers include acrylics (e.g. styrene acrylics), polyurethanes, polyesters, polyamides and vinyl copolymers. The second polymer can be an acrylic polymer. The acrylic polymer can be a copolymer of one or more acrylic monomer including n-butyl acrylate, n-butyl methacrylate, methyl methacrylate, ethyl methacrylate, and acrylic acid. The acrylic polymer can further include styrene monomer. Useful acrylic polymers include PD0659 and PD2056F, acrylic polymers available from H.B. Fuller Company (St. Paul, Minn.). The water based release coating includes up to around 50% by weight of the second polymer based on solids, up to about 40% by weight of the second polymer based on solids, or even up to about 30% by weight the second polymer based on solids.

The release coating can further include a colorant. The colorant makes it easier to see where the release coating has been applied. Useful colorants include FD & C colors which are certified and allowed by the United States for the Food, Pharmaceutical, Cosmetics & Personal Care Industry, including FD & C RED 40 and FD & C YELLOW 5 both available as water soluble dyes from Jagson Boya Kimya Dis Ticaret Limited STI (Istanbul, Turkey).

The release coating can also include additional components such as preservatives, UV additives and surfactants. A UV additive could offer an alternate way to see where the release coating has been applied. A useful UV additive includes BLANKOPHOR P150 LIQUID 01 available from Indulor America LP (Graham, N.C.).

The release coating should flow freely to provide easy application from its container.

It is desirable for the release coating to provide release properties shortly after application. Further, the release coating can maintain its release properties for an extended period. This enables the substrates to be prepared one day and then the audit performed at a later date. The release coating can provide release properties in less than about 10 minutes, less than about 5 minutes, or even in less than about 2 minutes after application. The release coating (after application) maintains its release properties for at least one day after application, at least one week after application, or even at least one month after application.

The adhesive should pull substantially cleanly from the release coating. By substantially cleanly it is meant that there is no visible adhesive residue remaining on the coated surface/removal of fibers from the surface and further that there is negligible transfer of release coating to the adhesive.

Release Coating Kit

The release coating of the present invention may be sold in the form of a kit including a container. The container can be e.g. a can, carton, bottle or wipe. The container is generally plastic but could alternately be made from metal or glass. When made from plastic, the container is selected from a group consisting of polyethylene (e.g. high density polyethylene, low density polyethylene, or medium density polyethylene) and polypropylene. Alternately, the container could be made from polyester, polystyrene or polyvinyl chloride (PVC).

The container can be a plastic bottle with an applicator at one end. The applicator can be a spray tip, a spout, a roller, a brush or a sponge. The bottle can be squeezable to assist in application Generally small containers enable easy transport and are more convenient. In some cases, the container holds no greater than about 20 ounces, no greater than 10 ounces, no greater than about 5 ounces, no greater than about 3.4 ounces, between about 2 ounces and about 20 ounces, or even between about 3 ounces and 10 ounces of the water based release coating. At times, a container that holds no greater than about 3.4 ounces is preferred to enable airplane transport in a carry on luggage bag.

When the release coating is a liquid at room temperature, a squeezable plastic bottle, holding no greater than about 10 ounces, with an applicator at one end is a preferred container as it provides an efficient way to apply a consistent coating.

The kit can include directions for use. Possible directions for use include directions for storage, for application, for performing an adhesive audit or any combination thereof. The directions can be in the form of a label on the container, in a package containing the container, on a sell sheet, on a website or in any other document teaching how store, apply or use the release coating.

The kit could optionally include a UV light. The UV light could be useful to see where the release coating is applied if the release coating includes a UV additive.

Method of Performing a Hot Melt Adhesive Audit

The invention further includes a method of performing an adhesive audit on a substrate, the method including obtaining a release coating that is liquid at room temperature, applying the release coating to substrate areas to be bonded, bonding the substrate through the substrate areas to be bonded, disassembling the substrate, removing the adhesive from the substrate with release coating, and weighing the adhesive removed to determine the amount applied per unit.

The release coating can be applied by a number of methods including wiping on the substrate with a cloth/brush or using an applicator equipped with a spray tip, spout, roller, brush or sponge. One pass with the applicator typically gives the required coverage.

In a preferred embodiment, the substrate includes cellulose. When used on a substrate including cellulose, very little drying time is needed. Once applied, a dry time of less than about 10 minutes, less than about 5 minutes, less than about 2 minutes, or even less that about 1 minute is all that is required.

Suitable substrates include virgin and recycled cellulose-based substrates including, e.g., paper, kraft paper, cover stock, paperboard, corrugated paperboard, cardboard, corrugated cardboard, chipboard, and solid fiber paper board, as well as the aforementioned substrates with treated surfaces including, e.g., coatings (e.g., coated Kraft paper, coated Kraft paperboard, and coated cardboard), film, laminates, foil, metallized surfaces, and combinations thereof.

The release coating composition is suitable for doing audits on production lines where adhesive compositions are used. An exemplary application includes but is not limited to use in filters (e.g., bonding a filter medium to a filter frame and maintaining pleats (i.e., folds) of a pleated filter media in a fixed, spaced apart relation to one another).

The release coating composition is particularly suitable for performing audits on lines where packaging constructions are assembled including, e.g., bags, boxes (e.g., beverage (e.g., beer, soda, etc), and cereal boxes), cartons, cases (e.g. carrying cases), trays, and combinations thereof, and sealing applications including, e.g., case and carton sealing.

The release coating is useful for performing audits with a wide range of adhesives including hot melt, water based, reactive hot melts, and solventless adhesives (e.g one and two part).

Suitable hot melt adhesives can be based on the following polymers: polyethylene, ethylene copolymers (e.g. ethylene vinyl acetate, metallocene catalyzed ethylene octene), polypropylene, propylene copolymers, amorphous poly alpha olefins (APAO), polyester, thermoplastic polyurethanes and polyamides.

EXAMPLES

Test Procedures

Test procedures used in the examples include the following.

Hot Melt Release Coating Adhesion Test

The Release Coating Adhesion Test is a useful lab test for determining how well different hot melt adhesives release from the release coating. Ideally, a variety of adhesives will release from the same release coating. A release coating could still be useful as long as at least one adhesive releases from it.
1. Apply one pass of a water based release coating to two similar sized pieces (typically around 6" by 4") of Rock Tenn 44 ECT Corrugated Board stock using a 2.5 oz applicator bottle equipped with a sponge tip (such as those used for shoe polish)
2. Allow coating to dry for at least 1 minute
3. Heat a pint can of the hot melt to be tested in an oven to its application temperature
4. Pour a bead (around ½" inch in width) of the molten hot melt onto the dried water based release coating of the first board. Pour length wise, horizontal to the 6" dimension of the board.
5. Immediately press the release coating facing side of the second board firmly into place using hand pressure.
6. After 5 minutes, pull the bond apart
7. Record the % fiber failure Application Ease When performing the Release Coating Adhesion Test, the application ease was noted by evaluating how easily the release coating flowed from the 2.5 oz applicator bottle equipped with a sponge tip. The release coating was then given one of the following ratings:
Easy—Easy to dispense
Acceptable—Flow not as smooth as Easy (above), but still acceptable
Poor—Difficult to dispense, poor flow

TABLE ONE

|  | Compar 1 | Ex. 1 | Ex. 2 | Ex. 3 | Ex. 4 | Ex. 5 | Ex. 6 |
|---|---|---|---|---|---|---|---|
| Michelman Release Coat 40 (wt %) |  |  |  |  |  |  | 100 |
| Michelman Release Coat 30 (wt %) |  | 12.5 | 25 | 40 | 50 | 100 |  |
| Water (wt %) | 100 | 87.5 | 75 | 60 | 50 |  |  |
| Solids (wt %) | 0 | 3.75 | 7.5 | 12 | 15 | 30 | 40 |
| Application Ease | Easy | Easy | Easy | Easy | Easy | Easy | Easy |
| Release Coating Adhesion Test to PHC9250 (% Fiber Tear) | 100 | 0 | 0 | 0 | 0 | 0 | 0 |

TABLE ONE-continued

|  | Compar 1 | Ex. 1 | Ex. 2 | Ex. 3 | Ex. 4 | Ex. 5 | Ex. 6 |
|---|---|---|---|---|---|---|---|
| Release Coating Adhesion Test to HM2835Y (% Fiber Tear) | 100 | 100 | 100 | 0 | 0 | 0 | 0 |
| Release Coating Adhesion Test to 3338E (% Fiber Tear) | 100 | 85 | 5 | 0 | 0 | 0 | 0 |

TABLE TWO

|  | Ex. 7 | Ex. 8 |
|---|---|---|
| Michelman Release Coat 30 (wt %) | 75 | 75 |
| PD2056F (60% solids) (wt %) | 25 |  |
| PD0659 (50% solids) (wt %) |  | 25 |
| Solids (wt %) | 37.5 | 35 |
| Application Ease | Poor | Acceptable |
| Release Coating Adhesion Test to PHC9250 (% Fiber Tear) | 0 | 0 |
| Release Coating Adhesion Test to HM2835Y (% Fiber Tear) | 0 | 0 |
| Release Coating Adhesion Test to 3338E (% Fiber Tear) | 0 | 0 |

PHC9250, HM2835Y and 3338E are all hot melt adhesives commercially available from HB Fuller Company (St. Paul, Minn.). For the Release Coating Adhesion Test, all three adhesives were applied at 350° F.

In Examples 9 and 10, the prior art adhesive audit method using Painter's tape was compared to the current invention using the release coating from Example 6 applied with one pass of a 2.5 oz applicator bottle equipped with a sponge tip (such as those used for shoe polish).

Example 9

The time needed to prepare a carton for an audit was recorded.

|  | Time to prepare carton for audit (seconds) |
|---|---|
| Prior art method Applying Painter's tape to areas to be bonded | 169 |
| Inventive method | 38 |

Example 10

The time needed to audit 9 case lines was recorded.

|  | Time to audit 9 lines (hours) |
|---|---|
| Prior art method Applying Painter's tape to areas to be bonded | 3 (estimate based on prior audits) |
| Inventive method | 1.5 |

Other embodiments are within the claims.

What is claimed is:

1. A method of performing an adhesive audit on a production line, the method comprising:
   a) obtaining a release coating that is liquid at room temperature,
   b) applying the release coating to substrate areas to be bonded,
   c) bonding the substrate, with a hot melt adhesive, through the substrate areas to be bonded to form a unit on a production line wherein the unit is a filter, bag, box, case, carton or tray,
   d) disassembling the unit,
   e) removing the adhesive from the substrate with release coating, and
   f) weighing the adhesive removed to determine the amount applied per unit.

2. The method of claim 1 wherein the release coating further comprises a colorant.

3. The method of claim 1, wherein the substrate comprises cellulose.

4. The method of claim 1 wherein the release coating is a water based release coating.

5. The method of claim 4 wherein the release coating comprises polydimethylsiloxane.

6. The method of claim 4 wherein the release coating has a solids content of less than 30% by weight.

7. The method of claim 1 wherein the release coating has release properties within 2 minutes after application and maintains those properties for at least one day.

8. The method of claim 1 wherein the release coating is applied by use of a container with an applicator at one end.

9. The method of claim 8 wherein the container holds no more than 3.4 ounces.

10. The method of claim 8 wherein the container comprises a plastic container equipped with a sponge applicator.

* * * * *